US006656678B1

(12) United States Patent
Wolf et al.

(10) Patent No.: US 6,656,678 B1
(45) Date of Patent: Dec. 2, 2003

(54) METHOD FOR EXAMINATION OF A SURFACE LAYER

(75) Inventors: Bernhard Wolf, Stegen (DE); Hans-Jürgen Gahle, Emmendingen (DE); Günter Igel, Teningen (DE); Werner Baumann, Bühl (DE); Ralf Ehret, Merdingen (DE); Mirko Lehmann, Freiburg (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/585,146

(22) Filed: Jun. 1, 2000

Related U.S. Application Data

(63) Continuation of application No. PCT/EP98/07597, filed on Nov. 25, 1998.

(30) Foreign Application Priority Data

Dec. 4, 1997 (DE) .......................... 197 53 790

(51) Int. Cl.⁷ .......................... C12Q 1/00; G01N 33/543
(52) U.S. Cl. .......................... 435/4; 436/518
(58) Field of Search .............................. 436/518; 435/4

(56) References Cited

U.S. PATENT DOCUMENTS

| | | | |
|---|---|---|---|
| 4,924,091 A | | 5/1990 | Hansma et al. |
| 5,031,099 A | * | 7/1991 | Kettler .................. 382/133 |
| 5,408,312 A | * | 4/1995 | Pries et al. ............. 250/228 |
| 5,442,443 A | | 8/1995 | Guerra |
| 5,510,628 A | | 4/1996 | Georger, Jr. et al. |
| 5,545,531 A | | 8/1996 | Rava et al. |
| 5,721,435 A | * | 2/1998 | Troll .................... 250/559.29 |
| 5,735,276 A | * | 4/1998 | Lemelson ................ 250/458.1 |
| 6,033,916 A | * | 3/2000 | Sieben et al. ........... 204/192.25 |
| 6,148,096 A | * | 11/2000 | Pressman et al. ........ 348/79 |
| 6,198,532 B1 | * | 3/2001 | Cabib et al. ............ 250/461.2 |
| 6,280,586 B1 | * | 8/2001 | Wolf et al. ............. 204/403.01 |

FOREIGN PATENT DOCUMENTS

| | | |
|---|---|---|
| DE | 285 534 A7 | 12/1990 |
| EP | 0 749 010 A2 | 12/1996 |

OTHER PUBLICATIONS

N. Streckfuss et al., "Analysis Of Trace Metals On Silicon Surfaces" *Fresenius' Journal of Analytical Chemistry* pp. 765–768, (1992).

* cited by examiner

*Primary Examiner*—Jon P. Weber
(74) *Attorney, Agent, or Firm*—Akin Gump Strauss Hauer & Feld, L.L.P.

(57) ABSTRACT

In a method for examination of the surface of an object for a topographic and/or a chemical property, the object-surface is impinged with surface-structure selective biocomponents for examination of a topographic property and/or with chemoselective biocomponents for the examination of a chemical property, together with a nutrient medium and/or an osmotic protective medium for the biocomponents. The biocomponents contained in the nutrient medium and/or the osmotic protective medium are in contact with the object-surface or are spaced from the object surface by less than the detection range of the biocomponents. The object surface is then examined with the biocomponents contained in the nutrient medium and/or the osmotic protective medium by determining at least one examination measurement value. The examination measurement value is compared with a reference measurement value, and conclusions can be drawn about the topographic and/or chemical properties of the object from the result of the comparison. Using the method, an object surface can be examined for a topographic and/or chemical property in a simple manner with a high measuring sensitivity.

11 Claims, No Drawings

METHOD FOR EXAMINATION OF A SURFACE LAYER

CROSS-REFERENCE TO RELATED APPLICATION

This application is a continuation of International Application No. PCT/EP98/07597 filed Nov. 25, 1998 the disclosure of which is incorporated herein by reference.

BACKGROUND OF THE INVENTION

The invention relates to a method for examination of the surface or the surface layer of an object for at least one topographic and/or chemical property.

A method already known from N. Streckfuβ, *Characterization of Silicon Surfaces Using X-ray Fluorescence Analysis under Total Reflection Conditions*, Shaker Publishers (1995), for determining the chemical composition of an object is the Auger method. In this method the surface of an object to be examined is bombarded with electron beams or irradiated with short-wave, energy-rich radiation, which release secondary electrons on the object surface. The energy of these secondary electrons is measured using a suitable sensor technology. From the measured energy, conclusions can then be drawn about the chemical composition of the object.

From U.S. Pat. No. 5,442,443 it is also known to determine the topography of a surface area of an object by tunnel microscopy. In this method a test point up to a few tenths of a nanometer is introduced onto the object. A voltage is applied on the test point towards the object surface. The test point is then moved along the object surface in a grid pattern, whereby the electric current flowing through the test point is measured, which is a measure for the distance of the test point from the object surface.

A disadvantage of the previously known methods consists in that they require a considerable equipment expense and their use is thus correspondingly expensive. Moreover, it is unfavorable that for the examination of topographic and chemical properties of the object, different techniques are necessary, which additionally increases the expense for the examination of the object. Moreover, the measurement sensitivity of the previously known methods is frequently not sufficient.

BRIEF SUMMARY OF THE INVENTION

Therefore, an object of the invention is to create a method, with which a surface or a surface layer of an object can be examined in a simple manner with high measurement sensitivity to a topographic and/or a chemical property.

This object is achieved in that the object-surface for examination of a topographic property is impinged with surface-structure selective biocomponents and/or for examination of a chemical property is impinged with chemoselective biocomponents, as well as with a nutrient medium and/or an osmotic protective medium for the biocomponents, in such a way that biocomponents present in the nutrient medium and/or the osmotic protective medium are in contact with the object-surface or are spaced from the object surface by less than the detection range of the biocomponents, in that the object surface is examined with the biocomponents present in the nutrient medium and/or the osmotic protective medium, such that at least one examination measurement value is determined, and in that the examination measurement value is compared with a reference measurement value, and from the result of the comparison conclusions are drawn about a chemical and/or a topographic property of the object.

DETAILED DESCRIPTION OF THE INVENTION

The biocomponents can be, for example, membrane-enclosed compartments, such as biological cells, isolated cell components, such as cellular membranes microorganisms (e.g., fungi, bacteria), antibodies, antigens, receptors, organelles, viruses, vesicles, micelles, or biomolecules. Optionally, the biocomponents can be specially designed for the detection of chemical and/or topographic properties.

In an advantageous manner, for the examination of a topographic or chemical property of an object, the capacity of biocomponents is thus used for reacting with a high degree of specificity to different topographic or chemical conditions caused evolutively. For this purpose, biocomponents are first brought into a nutrient medium and/or an osmotic protective medium on or in the vicinity of the object surface. Here, it is sufficient if at least one part of the biocomponents is spaced somewhat from the object surface, so that, for example, materials diffusing from the surface layer through the nutrient medium and/or the osmotic protective medium to the biocomponents and/or potential fields caused by the surface structure in the area of the object surface can be detected by the biocomponents. Depending on the topography and/or chemical composition of the surface layer, the biocomponents then develop into different forms, for example in color, shape and/or size, and/or arrange themselves differently on the surface. With the nutrient medium the biocomponents can be maintained vital over a longer time period, so that they have sufficient time available to adapt to the chemical and/or topographic object properties. The nutrient medium can be, for example, a nutrient liquid in which the biocomponents swim.

The object surface with the biocomponents is then optically examined, in that one or more examination measurement values are optically determined. These are then compared to reference measurement values, which are measured, for example, on an object having known surface topography and/or having known chemical properties. From the result of the comparison, conclusions are made about a topographic and/or chemical property of the object examined, in that, for example, in the case of an extensive agreement of measurement and reference measurement values, common features between the properties of the examined objects and those of the reference object are established, and with a clear deviation of the measurement values from the reference measurement values, differences between the properties of the examined object and the reference object are established.

The method according to the invention makes it possible to examine topographic and/or chemical properties of an object with a comparatively small equipment expense. In an advantageous manner, the same technology can be applied in the examination of topographic properties as in the examination of chemical object properties. The method can therefore be performed in a particularly cost-effective manner. In addition, the method exhibits a high measurement sensitivity, such that small changes or differences in the surface topography or in the chemical properties can be recognized immediately in real-time and online.

As biocomponents, for example, easily handled surface structure selective cells of the cell type LS 174 T or highly surface-selective tumor cells can be used.

A preferred embodiment of the invention provides that at least one part of the biocomponents is deposited on the object surface. The biocomponents are then constantly in contact with the surface layer of the object, so that they can react in a particularly sensitive manner to the chemical components contained in them and/or to the surface structure of the object.

It is advantageous if, after the impingement of the object surface with the nutrient medium and/or the osmotic protective medium and the biocomponents, examination measurement values are determined at at least two time points set apart in time. In this method, it is even possible that the measurement values determined in the individual time points are compared with different reference measurement values, in order to take into account time-dependent changes of the biocomponents. The measuring sensitivity of the method is additionally increased in this manner.

Expediently, at least one examination measurement value is optically-determined. The examination procedure can then be performed in a particularly simple manner.

A preferred embodiment of the invention provides that an optical image is recorded of the surface with the biocomponents and that the image is compared by optical image analysis with a reference image. It is thereby possible, for example, to determine in a simple manner, by methods of image processing, the distribution of the biocomponents located on or near the surface, in order to make conclusions about the structural properties or the material properties of the object. Thus, for example, in semiconductors the growth behavior of biological cells is different for differently processed ISFETs having the same surface. Consequently, by evaluation of the surface distribution of the cells deposited on the surface of a semiconductor, information can be obtained about the manufacturing method of the semiconductor.

By evaluation of the surface distribution of the biocomponents deposited on the object, chemical properties of an object can also be determined. Thus, for example, it has been revealed that cells of the cell type LS 174 T do not grow on ISFETs which have copper components.

It is advantageous if during the recording of the optical image on the surface and on these impinging biocomponents, an optical interference pattern is created, and if the image is compared to an interference reference image by optical image analysis. In this manner, the dimensions and the arrangement of the individual biocomponents located on or in the vicinity of the object surface can be determined in a particularly exact manner.

It is advantageous if at least one examination measurement value is determined using an electric, electronic or electrochemical sensor. Thus, for example, metabolic products of the biocomponents, gas contents and/or messenger substances can be determined by electrochemical ion concentration measurements. Thus, for example, the degree of the bonding of biological cells on the object surface can be established in a sensory manner via the metabolism. Furthermore, by potential measurements information can be obtained about the biocomponents. Since the living conditions of the biocomponents and thus their metabolism is influenced by the chemical and/or topographic properties of the surface layer of the object, the measurement signals obtained using the electric, electronic or electrochemical sensors allow conclusions to be reached about the properties of the surface layer.

An advantageous embodiment of the invention provides that at least one part of the biocomponents comprises at least structure-selective and/or chemoselective biocomponents that correspond to a growth, structure or functionmodulating material contained in the object to be examined. The method then has an even larger measurement sensitivity. Thus, for example, lacquer residues on a semiconductor can be detected thereby, since because of the toxicity to the biocomponents of the materials contained therein, the biocomponents do not grow there.

It is advantageous if the nutrient medium and/or the osmotic protective medium with the biocomponents contained therein is removed from the surface of the object after it is examined. After performing the method, no residues then remain on the object surface.

It is especially advantageous if the surface of an object made of non-biological material and/or a surface layer having such a material is impinged with the biocomponents as well as the nutrient and/or osmotic protective medium. Thus, for example, residues of thin lacquer layers, such as residues of resists for photostructuring can be localized on the surface of a wafer or like semiconductor or solid body. In this manner, discoveries can be made about the manufacturing method of the wafer, so that the manufacturing method can be optimized.

The invention relates, in addition, to a method for structuring a surface layer of an object.

From semiconductor technology, a method is already known for structuring a surface layer of a wafer, in which a light-sensitive photoresist emulsion is first applied on the surface of the wafer, which after exposure with ultraviolet light becomes insoluble and thereby resistant to a chemical, for example an acid. The emulsion applied on the wafer is then exposed by a photographic mask, whereby the mask covers those areas in which wafer material should be removed in a subsequent etching method for the structuring of the surface layer of the wafer. The emulsion masked in this manner is then developed. Then, the unexposed areas are removed with a solvent. As the next step, the wafer surface is brought into contact with an acid, wherein the photoresist-emulsion protects those areas in which a removal of surface material by etching is not desired. Finally, the photoresist material is removed from the surface.

The previously known method has many method steps and requires a considerable equipment expense. It is therefore comparatively costly and expensive, which is seen as disadvantageous in the serial production of objects to be structured, for example of wafers. Furthermore, the handling of acids is associated with health risks for the personnel involved in the performance of the method, and therefore requires corresponding precautions.

Therefore, an object of the invention is to create a method for structuring a surface layer of an object, which can be executed in a simple and cost-effective manner.

This object is achieved in that on the surface of the object, biocomponents that remove surface material are applied in a nutrient medium and/or an osmotic protective medium, and in that the nutrient medium and/or the osmotic protective medium are removed with the biocomponents contained therein after the removal of surface material from the object surface. The surface layer of the object can thus be roughened or otherwise structurally changed in a simple manner.

It is especially advantageous if the biocomponents are deposited on the object surface in an adherent manner. A surface structuring corresponding to the arrangement of the deposited biocomponents then results on the surface layer.

An advantageous embodiment of the method provides that material-selective biocomponents are used, which are specialized for the removal of one or more materials contained in the object. It is therefore possible, for example, to intentionally remove certain impurities on the surface layer of the object and thus to clean the object. Also, the chemical composition of the surface layer can be changed by the intentional removal of certain materials.

The above-mentioned object can also be achieved in a method for structuring a surface layer of an object, in that biocomponents which separate out a precipitation product are adherently deposited on the surface of the object in a nutrient medium and/or an osmotic protective medium, and in that the nutrient medium and/or the osmotic protective medium with the biocomponents contained therein are removed after the separation of the precipitation product from the object surface.

The object surface can thus be provided in a simple manner with a structure and/or a coating and thus be changed both materially and structurally. With the nutrient medium biocomponents can be maintained vital over a longer time period, so that they have sufficient time available to separate out the precipitation product. With the method it is particularly possible to change the electric parameters of the object material, which is especially advantageous in semiconductor technology. Thus, for example, a cell culture can be deposited on the surface of the object, which precipitates out proteins, analytics and/or pigments, which become settled on the object surface. After the removal of the cell culture, a structuring formed by the precipitation product of the cell culture then remains on the surface layer of the object.

The aforementioned object can also be solved in a method for structuring a surface layer of an object, in that for forming a surface structure, biocomponents in a nutrient medium and/or an osmotic protective medium are deposited adherently on the surface of the object, and in that the nutrient medium and/or the osmotic protective medium are removed from the object surface after depositing of the biocomponents. Thus, for example, cells which function as a dielectric can be deposited on a semiconductor. With the nutrient medium and/or the osmotic protective medium the biocomponents can be maintained vital over a longer time period, so that they have sufficient time available to deposit on the object surface.

In the above method for structuring a surface layer of an object, it is even possible that biocomponents are used for the depositing the biocomponents on an area of a surface layer which exhibits a certain structure. With an object having a locally variable surface structure, the biocomponents then settle only at certain places of the surface. In an advantageous manner, it is thus possible to structure only certain areas of a surface layer without the use of a mask, while the remaining areas of the surface layer are left unchanged. Thus, for example, in the manufacture of a wafer the wafer surface can be constructed in such a manner that the biocomponents settle only at certain places, in order to form there a dielectric and/or to structure a surface area of the wafer, for example.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A method for examination of a surface or surface layer of an object for at least one of a chemical and topographic property, the surface or surface layer having unknown chemical or topographic properties, the method comprising:

impinging the object surface with at least one of a known surface-structure selective biocomponent for examination of a topographic property and a known chemoselective biocomponent for examination of a chemical property, the at least one biocomponent being contained in at least one of a nutrient medium and an osmotic protective medium, the at least one of a nutrient medium and an osmotic protective medium being in contact with the object surface;

examining the unknown object surface with the at least one biocomponent contained in the at least one nutrient medium and the osmotic protective medium to determine at least one examination measurement value;

comparing the at least one examination measurement value with at least one reference measurement value; and determining chemical or topographic characteristics of the originally unknown object surface from a result of the comparison.

2. The method according to claim 1, wherein at least a portion of the at least one biocomponent is deposited on the object surface.

3. The method according to claim 1, further comprising:

determining examination measurement values at at least two time points set apart in time after impinging the object surface with the at least one biocomponent being contained in at least one of a nutrient medium and an osmotic protective medium.

4. The method according to claim 1, wherein the at least one examination measurement value is optically determined.

5. The method according to claim 1, further comprising:

recording an optical image of the object surface with the at least one biocomponent; and comparing the optical image using optical image analysis with a reference image.

6. The method according to claim 5, further comprising:

creating an optical interference pattern during recording of the optical image of the at least one impinging biocomponent; and comparing the optical image with a reference interference image using optical image analysis.

7. The method according to claim 1, wherein the at least one examination measurement value is determined using an electric or electronic sensor.

8. The method according to claim 1, wherein at least a portion of the at least one biocomponent comprises a structure-selective or chemoselective biocomponent corresponding to at least one growth, structure or function-modulating material contained in the object to be examined.

9. The method according to claim 1, further comprising:

removing the at least one biocomponent having the at least one nutrient medium and osmotic protective medium after examination of the object surface.

10. The method according to claim 1, wherein the object surface or surface layer impinged by the at least one biocomponent containing the at least one nutrient and osmotic protective medium is made of a non-biological material.

11. The method according to claim 1, wherein the object surface impinged by the at least one biocomponent containing the at least one nutrient and osmotic protective medium comprises a solid body.

* * * * *